United States Patent

Ma et al.

(10) Patent No.: US 7,923,403 B2
(45) Date of Patent: Apr. 12, 2011

(54) METHOD FOR PREPARING CATALYSTS SUPPORTED ON CARBON NANOTUBES NETWORKS

(75) Inventors: Jun Ma, Lexington, MA (US); David Moy, Winchester, MA (US); Alan Fischer, Cambridge, MA (US); Robert Hoch, Hensonville, NY (US)

(73) Assignee: Hyperion Catalysis International, Inc., Cambridge, MA (US)

( * ) Notice: Subject to any disclaimer, the term of this patent is extended or adjusted under 35 U.S.C. 154(b) by 72 days.

(21) Appl. No.: 11/841,733

(22) Filed: Aug. 20, 2007

(65) Prior Publication Data

US 2008/0176740 A1    Jul. 24, 2008

Related U.S. Application Data

(63) Continuation of application No. 11/281,811, filed on Nov. 16, 2005, now abandoned.

(60) Provisional application No. 60/628,469, filed on Nov. 16, 2004.

(51) Int. Cl.
*B01J 21/18* (2006.01)
*B01J 23/00* (2006.01)
*B01J 23/40* (2006.01)
*B01J 23/74* (2006.01)

(52) U.S. Cl. ........ 502/185; 502/182; 502/184; 977/742; 977/745; 977/748; 977/750; 977/752

(58) Field of Classification Search .................. 502/182, 502/184, 185; 977/742, 745, 748, 750, 752
See application file for complete search history.

(56) References Cited

U.S. PATENT DOCUMENTS

| | | | |
|---|---|---|---|
| 4,663,230 | A | 5/1987 | Tennent et al. |
| 5,165,909 | A | 11/1992 | Tennent et al. |
| 5,171,560 | A | 12/1992 | Tennent et al. |
| 5,424,054 | A | 6/1995 | Bethune et al. |
| 5,456,897 | A | 10/1995 | Moy et al. |
| 5,500,200 | A | 3/1996 | Mandeville et al. |
| 5,569,635 | A | 10/1996 | Moy et al. |
| 5,691,054 | A | 11/1997 | Tennent et al. |
| 5,707,916 | A | 1/1998 | Snyder et al. |
| 5,965,470 | A | 10/1999 | Bening et al. |
| 6,031,711 | A | 2/2000 | Tennent et al. |
| 6,099,965 | A | 8/2000 | Tennent et al. |
| 6,143,689 | A | 11/2000 | Moy et al. |
| 6,203,814 | B1 | 3/2001 | Fisher et al. |
| 6,333,016 | B1 | 12/2001 | Resasco et al. |
| 6,761,870 | B1 | 7/2004 | Smalley et al. |

(Continued)

FOREIGN PATENT DOCUMENTS

WO      8907163 A1    8/1989

(Continued)

OTHER PUBLICATIONS

Written Opinions for PCT/US2005/041603 and PCT/US2005/041605.*

(Continued)

*Primary Examiner* — Patricia L Hailey (57) ABSTRACT

A new method for preparing a supported catalyst is herein provided. The supported catalyst comprises a carbon nanotube network structure containing metal catalysts. The metal catalyst may be loaded onto functionalized carbon nanotubes before forming the carbon nanotube network structure. Alternatively, the metal catalyst may be loaded onto the carbon nanotube network structures themselves.

11 Claims, 1 Drawing Sheet

U.S. PATENT DOCUMENTS

| | | | |
|---|---|---|---|
| 7,081,429 B2* | 7/2006 | Kishi et al. | 502/182 |
| 2002/0121460 A1* | 9/2002 | Moy et al. | 208/133 |
| 2003/0039604 A1 | 2/2003 | Niu et al. | |
| 2003/0086858 A1 | 5/2003 | Niu et al. | |
| 2003/0180526 A1* | 9/2003 | Winey et al. | 428/323 |
| 2003/0181526 A1 | 9/2003 | Bhagwat et al. | |
| 2006/0142149 A1* | 6/2006 | Ma et al. | 502/185 |
| 2008/0031802 A1 | 2/2008 | Ma et al. | |

FOREIGN PATENT DOCUMENTS

| | | | |
|---|---|---|---|
| WO | 9105089 A1 | | 4/1991 |
| WO | 9507316 A1 | | 3/1995 |
| WO | 9732571 A1 | | 9/1997 |
| WO | 0107694 A1 | | 2/2001 |
| WO | 02095098 A1 | | 11/2002 |
| WO | 2006/055670 | * | 5/2006 |
| WO | 2006/060168 | * | 8/2006 |
| WO | 2006135439 A2 | | 12/2006 |

OTHER PUBLICATIONS

Baker and Harris, Chemistry and Physics of Carbon, Walker and Thrower ed., vol. 14, 1978, p. 83.

Bethune, D. S., et al., "Cobalt-catalysed growth of carbon nanotubes with single-atomic-layer walls," Nature, vol. 363, pp. 605-607 (1993).

Dai., et al., "Single-Wall Nanotubes Produced by Metal-Catalyzed Disproportionation of Carbon Monoxide", Chemical Physics Letters 260: 471-475 (1996).

de Heer, Walt A., "Nanotubes and the Pursuit of Applications," MRS Bulletin, Apr. 2004.

Georgakilas, V., et al., "Organic Functionalization of Carbon Nanotubes", JACS Communications, 124, pp. 760-761 (2002).

Guo, T., et al., "Catalytic growth of single-walled nanotubes by laser vaporization" Chem. Phys. Lett. vol. 243: Issues 1-2: pp. 49-54 (1995).

Hirsch and Vostrowsky, "Functionalization of Carbon Nanotubes," Topics in Current Chemistry, 245:193-237 (2005).

Holzinger, M., et al., "[2+1] cycloaddition for cross linking SWCNTs", Carbon 42, pp. 941-947 (2004).

Iijima, S., "Helical microtubules of graphitic carbon," Nature 354:56-58 (1991).

Iijima, S. and Ichihashi,T. "Single-shell carbon nanotubes of 1-nm diameter", Nature, vol. 363, pp. 603-605(1993).

Kitiyanan, B., "Controlled production of single-wall carbon nanotubes by catalytic decomposition of CO on bimetallic Co-Mo catalysts," Chemical Physics Letters, 317, pp. 497-503 (2000).

Oberlin, A. & Endo, M., "Filamentous Growth of Carbon Through Benzene Decomposition," J. of Crystal Growth, vol. 32, pp. 335-349 (1976).

Rodriguez, N., "A Review of Catalytically Grown Carbon Nanofibers," J. Mater. Research, vol. 8, pp. 3233-3250 (1993).

Thess, A., et al., "Crystalline Ropes of Metallic Carbon Nanotubes," Science, 273:483-487 (1996).

Toebes, M.L., et al., "Synthesis and characterization of carbon nanofiber supported ruthenium catalysts", in Studies in Surface Science and Catalysis, vol. 143, pp. 202-208 (2002).

Weaver, J.H., "Totally Tubular," Science 265, pp. 611-612 (1994).

Hoch, et al., U.S. Appl. No. 10/875,435, "Functionalized Single Walled Carbon Nanotubes," filed Jun. 23, 2004.

* cited by examiner

Figure 1

METHOD FOR PREPARING CATALYSTS SUPPORTED ON CARBON NANOTUBES NETWORKS

CROSS REFERENCE INFORMATION

This application is a continuation of U.S. Ser. No. 11/281,811, filed Nov. 16, 2005, which claims benefit to and priority of U.S. Provisional Application No. 60/628,469, filed Nov. 16, 2004, each of which is hereby incorporated by reference in its entirety.

FIELD OF THE INVENTION

The invention relates to a composition of supported catalyst comprising networks of carbon nanotubes. The catalysts or catalyst precursor may be predeposited onto the carbon nanotube followed by formation of the carbon nanotube network structure with the predeposited or metal loaded carbon nanotube. Alternatively, the catalysts or catalyst precursor may be deposited onto the carbon nanotube after the formation of the carbon nanotube network structure. Whether the catalyst is deposited prior to or after the formation of the carbon nanotube network structure, the result of the present invention is a supported catalyst comprising a carbon nanotube network structure with metal catalysts more evenly and thoroughly dispersed in the structure. As such, the supported catalyst of the present invention contains a higher concentration and better distribution of metal catalysts, leading to more efficient and higher yields of the desired final product.

BACKGROUND OF THE INVENTION

Supported Catalysts

Supported catalysts (i.e., catalysts which are supported on some sort of surface, structure, or support, etc.) typically comprise an inert support material and a catalytically active material. Because heterogeneous reactions are normally carried out at elevated temperatures (and sometimes at elevated pressures as well) and in a reactive atmosphere, the exact chemical nature of the active catalyst component within the reaction zone can be difficult to determine. Thus, the terms "catalyst" or "supported catalyst" are often used interchangeably in the industry to refer to the composition comprising both the inert support and catalytically active material that is charged into the reaction zone.

Supported catalysts may be prepared by, for example, initially depositing precursors of the actual catalytically active material onto the inert support and then treating them accordingly (e.g., calcination), before feeding them into the reaction zone. More extensive pre-treatments and passivation steps to stabilize the supported catalyst before feeding to the reaction zone are also common. In a common example, metal salts are deposited onto inert support, converted into metal oxides by calcinations at elevated temperatures and then further reduced in situ to active pure metal catalysts.

Supported catalysts are widely used in heterogeneous catalytic reactions for chemical processes in the petroleum, petrochemical and chemical industries. Such reactions are commonly performed with the reactant(s) and product(s) in the fluid phase and the catalyst in the solid phase. In heterogeneous catalytic reactions, the reaction occurs at the interface between the phases, i.e., the interface between the fluid phase of the reactant(s) and product(s) and the solid phase of the supported catalyst. Hence, the properties of the surface of a heterogeneous supported catalyst are important factors in the effective use of the catalyst.

For example, the surface area of the active catalyst, as supported, and the accessibility of that surface area to reactant adsorption and product desorption are important. These factors affect the activity of the catalyst, i.e., the rate of conversion of reactants to products.

Generally, catalytic activity is proportional to catalyst surface area. Therefore, a high specific area is desirable. However, the surface area should be accessible to reactants and products as well as to heat flow. The chemisorption of a reactant by a catalyst surface is preceded by the diffusion of that reactant through the internal structure of the catalyst.

The active catalyst material may be supported on the external and/or internal structure of a support. Often, the internal structure of a support in the form of a porous structure can contain a greater surface area than the external surface. Therefore, when an ample amount of active catalysts are located or supported in the internal structure of a support, the accessibility of the internal structure of the support to reactant(s), product(s) and heat flow is important. Accessibility is measured by porosity and pore size distribution. Activated carbons and charcoals used as catalyst supports may have surface areas of about a thousand square meters per gram, and porosities of greater than 1 ml/gm. However, much of this surface area and porosity (e.g., as much as 50%, and often more), is associated with micropores (i.e., pores with pore diameters of 2 nm or less). These pores can be inaccessible because of diffusion limitations. They are easily plugged and thereby deactivated. Thus, high porosity materials where the pores are mainly in the mesopore region (i.e., 2-50 nm) or macropore region (i.e., greater than 50 nm) are most desirable.

It is also important that supported catalysts not fracture or attrit during use because such fragments may become entrained in the reaction stream and must then be separated from the reaction mixture. The cost of replacing attritted catalyst, the cost of separating it from the reaction mixture and the risk of contaminating the product are all burdens upon the process. In slurry phase, e.g., where the solid supported catalyst is filtered from the process stream and recycled to the reaction zone, the attritted fines may plug the filters and disrupt the process.

The chemical purity of the catalyst and the catalyst support also have important effects on the selectivity of the catalyst, i.e., the degree to which the catalyst produces one product from among several products, and the life of the catalyst.

It is also important that a catalyst, at the very least, minimize its contribution to the chemical contamination of reactant(s) and product(s). In the case of a catalyst support, this is even more important since the support is a potential source of contamination both to the catalyst it supports and to the chemical process. Further, some catalysts are particularly sensitive to contamination that can either promote unwanted competing reactions, i.e., affect its selectivity, or render the catalyst ineffective, i.e., "poison" it. For example, charcoal and commercial graphites or carbons made from petroleum residues usually contain trace amounts of sulfur or nitrogen. Carbons of agricultural origin may contain these contaminants as well as metals common to biological systems and may be undesirable for that reason.

Another important factor which can affect the efficiency of a supported catalyst is the amount of active catalysts in or on the support, as well as the distribution of the active catalysts throughout or within the support itself. Supported catalyst which contain more active catalysts in or on the support will generally have better results and catalytic activity than supported catalyst mainly comprised of the support material with few active catalysts. Furthermore, supported catalysts which have catalytic materials more evenly dispersed throughout or within the support generally have higher yield and catalytic activity than supported catalysts which have poor distribution of the catalytic material in or on the support.

Carbon Nanotubes

Carbon nanotubes have been identified as materials of interest for use as catalysts and catalyst supports. Carbon nanotubes exist in a variety of forms and have been prepared through the catalytic decomposition of various carbon-containing gases at metal surfaces.

Carbon nanotubes (also known as fibrils) are vermicular carbon deposits having diameters less than $1.0\mu$, preferably less than $0.5\mu$, and even more preferably less than $0.2\mu$. Carbon nanotubes can be either multi walled (i.e., have more than one graphene layer more or less parallel to the nanotube axis) or single walled (i.e., have only a single graphene layer parallel to the nanotube axis). Other types of carbon nanotubes are also known, such as fishbone fibrils (e.g., wherein the graphene sheets are disposed in a herringbone pattern with respect to the nanotube axis), etc. As produced, carbon nanotubes may be in the form of discrete nanotubes, aggregates of nanotubes (i.e., dense, microscopic particulate structure comprising entangled carbon nanotubes) or a mixture of both.

Processes for forming carbon nanotubes are well known. E.g., Baker and Harris, *Chemistry and Physics of Carbon*, Walker and Thrower ed., Vol. 14, 1978, p. 83; Rodriguez, N., *J. Mater. Research*, Vol. 8, p. 3233 (1993); Oberlin, A. and Endo, M., *J. of Crystal Growth*, Vol. 32 (1976), pp. 335-349; U.S. Pat. No. 4,663,230 to Tennent et al.; U.S. Pat. No. 5,171,560 to Tennent et al.; Iijima, Nature 354, 56, 1991; Weaver, Science 265, 1994; de Heer, Walt A., "Nanotubes and the Pursuit of Applications," *MRS Bulletin*, April, 2004; etc; "Single-shell carbon nanotubes of 1-nm diameter", S Iijima and T Ichihashi *Nature*, vol. 363, p. 603 (1993); "Cobalt-catalysed growth of carbon nanotubes with single-atomic-layer walls," D S Bethune, C H Kiang, M S DeVries, G Gorman, R Savoy and R Beyers *Nature*, vol. 363, p. 605 (1993); U.S. Pat. No. 5,424,054 to Bethune et al.; Guo, T., Nikoleev, P., Thess, A., Colbert, D. T., and Smally, R. E., Chem. Phys. Lett. 243: 1-12 (1995); Thess, A., Lee, R., Nikolaev, P., Dai, H., Petit, P., Robert, J., Xu, C., Lee, Y. H., Kim, S. G., Rinzler, A. G., Colbert, D. T., Scuseria, G. E., Tonarek, D., Fischer, J. E., and Smalley, R. E., Science, 273: 483-487 (1996); Dai., H., Rinzler, A. G., Nikolaev, P., Thess, A., Colbert, D. T., and Smalley, R. E., Chem. Phys. Lett. 260: 471-475 (1996); U.S. Pat. No. 6,761,870 (also WO 00/26138) to Smalley, et. al; "Controlled production of single-wall carbon nanotubes by catalytic decomposition of CO on bimetallic Co-Mo catalysts,"*Chemical Physics Letters,* 317 (2000) 497-503; U.S. Pat. No. 6,333,016 to Resasco, et. al., etc. All of these references are hereby incorporated by reference.

The most preferred way of making carbon nanotubes is by catalytic growth from hydrocarbons or other gaseous carbon compounds, such as CO, mediated by supported or free floating catalyst particles.

Carbon nanotubes may also be formed as aggregates, which are dense microscope particulate structures of entangled carbon nanotubes and may resemble the morphology of bird nest, cotton candy, combed yarn or open net. Aggregates are formed during the production of carbon nanotubes and the morphology of the aggregate is controlled by the choice of catalyst support. Spherical supports grow nanotubes in all directions leading to the formation of bird nest aggregates. Combed yarn and open net aggregates are prepared using supports having one or more readily cleavable planar surfaces, e.g., an iron or iron-containing metal catalyst particle deposited on a support material having one or more readily cleavable surfaces and a surface area of at least 1 square meter per gram. Further details regarding the formation of carbon nanotube aggregates may be found in the disclosure of U.S. Pat. No. 6,143,689 to Moy; U.S. Pat. No. 5,165,909 to Tennent; U.S. Pat. No. 5,456,897 to Moy et al.; Snyder et al., U.S. Pat. No. 5,707,916, filed May 1, 1991, and PCT Application No. US89/00322, filed Jan. 28, 1989 ("Carbon Fibrils") WO 89/07163, and Moy et al., U.S. Pat. No. 5,456,897 filed Aug. 2, 1994 and PCT Application No. US90/05498, filed Sep. 27, 1990 ("Battery") WO 91/05089, and U.S. Pat. No. 5,500,200 to Mandeville et al., filed Jun. 7, 1995 and U.S. Pat. No. 5,456,897 filed Aug. 2, 1994 and U.S. Pat. No. 5,569,635 filed Oct. 11, 1994 by Moy et al., all of which are assigned to the same assignee as the invention here and are hereby incorporated by reference.

Carbon nanotubes are distinguishable from commercially available continuous carbon fibers. For instance, carbon fibers have aspect ratios (L/D) of at least $10^4$ and often $10^6$ or more, while carbon nanotubes have desirably large, but unavoidably finite, aspect ratios (e.g., less than or greater than 100). Furthermore, the diameter of continuous carbon fibers, which is always greater than $1.0\mu$ and typically 5 to $7\mu$, is also far larger than that of carbon nanotubes, which is usually less than $1.0\mu$. Carbon nanotubes also have vastly superior strength and conductivity than carbon fibers.

Carbon nanotubes also differ physically and chemically from other forms of carbon such as standard graphite and carbon black. Standard graphite, because of its structure, can undergo oxidation to almost complete saturation. Moreover, carbon black is an amorphous carbon generally in the form of spheroidal particles having a graphene structure, such as carbon layers around a disordered nucleus. On the other hand, carbon nanotubes have one or more layers of ordered graphitic carbon atoms disposed substantially concentrically about the cylindrical axis of the nanotube. These differences, among others, make graphite and carbon black poor predictors of carbon nanotube chemistry.

Carbon Nanotube Structures

In addition to carbon nanotubes, carbon nanotube structures are known to be useful catalyst supports and catalysts. Carbon nanotube structures provide certain structural advantages over other known carbon catalyst supports in that more of the internal pore structures are in the form of mesopores (i.e., 2 to 50 nm) and macropores (i.e., greater than 50 nm). Furthermore, carbon nanotube structures also have greater structural strength, and thus is less likely to frit or attrit in comparison to other known carbon catalyst supports.

Carbon nanotube structures include, but are not limited to the following groups: assemblages, networks and rigid porous structures.

a. Assemblages are carbon nanotube structures which have relatively uniform properties along one, preferably two and most desirably three dimensional axis of the three dimensional assemblage. (E.g., U.S. Pat. No. 5,691,054 hereby incorporated by reference). Generally, assemblages (including but not limited to mats and plugs) are formed by de-aggregating carbon nanotube aggregates, and then reassembling them to form assemblages which have uniform properties over a greater range of distance than the original aggregates. Nanotube mats or assemblages have been prepared by dispersing carbon nanotubes in aqueous or organic mediums and then filtering the nanotubes to form a mat or assemblage. Mats and plugs have also been prepared by forming a gel or paste of nanotubes in a fluid, e.g. an organic solvent such as propane and then heating the gel or paste to a temperature above the critical temperature of the medium, removing the supercritical fluid and finally removing the resultant porous mat or plug from the vessel in which the process has been carried out. A gluing agent may be present during the step of mat or plug formation. As the assemblage dries, the glue will concentrate at the nanotube intersections. Preferred gluing agents or binders include cellulose-based polymers, hydroxyl ethyl cellulose, carboxyl methyl cellulose, cellulose, carbohydrates, polyethylene, polystyrene, nylon, polyurethane, polyester, polyamides, poly(dimethylsiloxane), acrylic polymers and phenolic resins. Preferably, the polymers are free of alkali metal salts such as sodium or potassium salts.

b. Networks are formed by linking individual functionalized carbon nanotubes (i.e., carbon nanotubes which contain functional groups, such as but not limited to oxygen containing moieties, on their surface) together by using a linking molecule between the functionalized groups located on the surface of the carbon nanotubes. (E.g., PCT/US97/03553 or WO 97/32571, hereby incorporated by reference). The carbon nanotubes are functionalized, for example, by contacting them with an appropriate reagent such as those described in WO 97/32571 or U.S. Pat. No. 6,203,814, all of which are incorporated by reference. Alternatively, the carbon nanotubes are functionalized through oxidation with oxidizing agents such as potassium chlorate ($KClO_3$), sulfuric acid ($H_2SO_4$), nitric acid ($HNO_3$), hydrogen peroxide ($H_2O_2$), $CO_2$, $O_2$, steam, $N_2O$, NO, $NO_2$, $O_3$, $ClO_2$, etc. (e.g. U.S. Pat. No. 5,965,470, WO 95/07316, PCT/US00/18670 or WO 01/07694, all of which are herein incorporated by reference). Typical linking molecules or linking agents are bifunctional compounds such as diamines, diols, etc.

c. Rigid porous structures are formed by either linking the individual functionalized carbon nanotubes together without the use of a linking molecule, or by gluing carbon nanotube aggregates together with a gluing agent. U.S. Pat. No. 6,099,965, hereby incorporated by reference, discloses that functionalized nanotubes become self adhesive after an appropriate thermal treatment. The carbon nanotubes are functionalized, for example, by contacting them with an appropriate reagent (e.g., WO 97/32571, U.S. Pat. No. 6,203,814, all of which are herein incorporated by reference), or by contacting them with an oxidizing agent such as potassium chlorate ($KClO_3$), sulfuric acid ($H_2SO_4$), nitric acid ($HNO_3$), persulfate, hydrogen peroxide ($H_2O_2$), $CO_2$, $O_2$, steam, $N_2O$, NO, $NO_2$, $O_3$, $ClO_2$, etc. (e.g., U.S. Pat. No. 5,965,470, WO 95/07316, PCT/US00/18670 or WO 01/07694, all of which are herein incorporated by reference). The oxidized nanotubes are believed to form ester, anhydride, lactone and ether bonds between themselves.

It is useful to note that assemblages and rigid porous structures as defined above, are essentially "pure nanotubes" admixed, at most with a minor amount of gluing agent. Networks, on the other hand, because of the presence of the "linker" and the availability of linker molecules of various molecular weights and structures provide an additional degree of control on the properties of the final structure. In particular, density and porosity can be tailored.

To be useful as catalyst supports, the structures above must be formed into generally accepted forms of industrial catalyst by methods such as pelletization, extrusion, compaction or powder agglomeration. See, for example. "Catalyse de Contact" edited by J. F. Le Page, Paris, 1978, hereby incorporated by reference. Rigid porous structures may advantageously be made by extruding a paste like suspension of functionalized nanotubes or a mixture of as made aggregates and gluing agent, (optionally admixed with a liquid vehicle) followed by a calcinations step to drive off conveying liquids and either cross link the functionalized nanotubes or to pyrolize the gluing agent.

While activated charcoals and other materials have been used as catalysts and catalyst supports, none have heretofore had all of the requisite qualities of high surface area, porosity, pore size distribution, resistance to attrition and purity for the conduct of a variety of selected petrochemical and refining processes as compared to carbon nanotube structures. Furthermore, unlike carbon nanotube structures, much of the surface area in activated charcoals and other materials is in the form of inaccessible micropores.

Therefore, it would be desirable to provide a supported catalyst comprising a carbon nanotube structure with well or evenly dispersed metal catalysts therein, the supported catalyst consequently having highly accessible surface area, high porosity, and attrition resistance, and which are substantially micropore free, highly active, highly selective and are capable of extended use with no significant deactivation.

SUMMARY OF THE INVENTION

A new method for preparing supported catalysts is provided comprising the steps of loading metal catalyst onto carbon nanotubes to form metal loaded carbon nanotubes; and forming a carbon nanotube network structure from said metal loaded carbon nanotubes.

Another new method for preparing supported catalysts is also provided comprising the steps of forming a carbon nanotube network structure and then loading metal catalyst onto said carbon nanotube network structure.

Preferably, the carbon nanotube network structures are prepared by a process comprising the steps of functionalizing carbon nanotubes with a functionalizing agent to form functionalized carbon nanotubes, and adding an appropriate reagent to said functionalized carbon nanotubes to form a carbon nanotube network structure. These reagents are linking molecules such as diamines or diols which hold the functionalized carbon nanotubes together. The metal catalyst catalysts may be loaded onto the carbon nanotubes prior to forming the carbon nanotube network structure or may be loaded onto the carbon nanotube network structure after it has been formed.

The most straightforward functionalization, especially for multi walled carbon nanotubes, is oxidation. Useful oxidizing agents include, but is not limited to, potassium chlorate, sulfuric acid, nitric acid ($HNO_3$), persulfate, hydrogen peroxide ($H_2O_2$), $CO_2$, $O_2$, steam, $N_2O$, NO, $NO_2$, $O_3$, or $ClO_2$.

Catalysts or catalyst precursors useful in the methods of the present invention include, but are not limited to, metals such as ruthenium, osmium, rhodium, iridium, palladium, platinum or a mixture thereof, as well as metal oxides, metal halides, metal carbides, metal nitrides, metal phosphides and metal sulfides of other transition metals including but not limited to Ti, V, Cr, Mn, Fe, Co, Ni, Cu, Zn, Y, Zr, Nb, Mo, La, Ce, W or combinations thereof. The metal catalysts or metal catalyst precursors may be loaded onto the nanotubes by any known method, such as ion exchange, impregnation, or incipient wetness, precipitation, physical or chemical adsorption or co-precipitation. In an exemplary embodiment, the metal catalysts are predeposited or loaded onto the functionalized carbon nanotubes by ion exchange, i.e. mixing a solution containing salts of said metal catalysts with the functionalized carbon nanotubes, allowing the salts to react with the functional groups of the functionalized nanotubes and evaporating the remaining solution (e.g. the excess solvent from the solution ). Alternatively, the metal catalysts are predeposited or loaded onto carbon nanotubes by impregnation, or incipient wetness, i.e. wetting a mass of carbon nanotubes with a solution of metal salts and evaporating the solvent. Alternatively, metal salts may be caused to precipitate from solution in the presence of a mass of carbon nanotubes causing said precipitated metal salts to physically or chemically adsorb on said nanotubes, followed by evaporation of the solvent.

In another exemplary embodiment, these same loading or deposition steps (e.g., ion exchange, impregnation, incipient wetness, precipitation, etc.) may be used to load or deposit the metal catalysts onto the carbon nanotube network structure after it has been formed.

Other improvements which the present invention provides over the prior art will be identified as a result of the following description which sets forth the preferred embodiments of the present invention. The description is not in any way intended to limit the scope of the present invention, but rather only to provide a working example of the present preferred embodiments. The scope of the present invention will be pointed out in the appended claims.

BRIEF DESCRIPTION OF THE DRAWINGS

The accompanying drawings, which are incorporated in and constitute a part of the specification, illustrate an exemplary embodiment of the present invention.

DETAILED DESCRIPTION OF PREFERRED EMBODIMENTS

Figure 1:
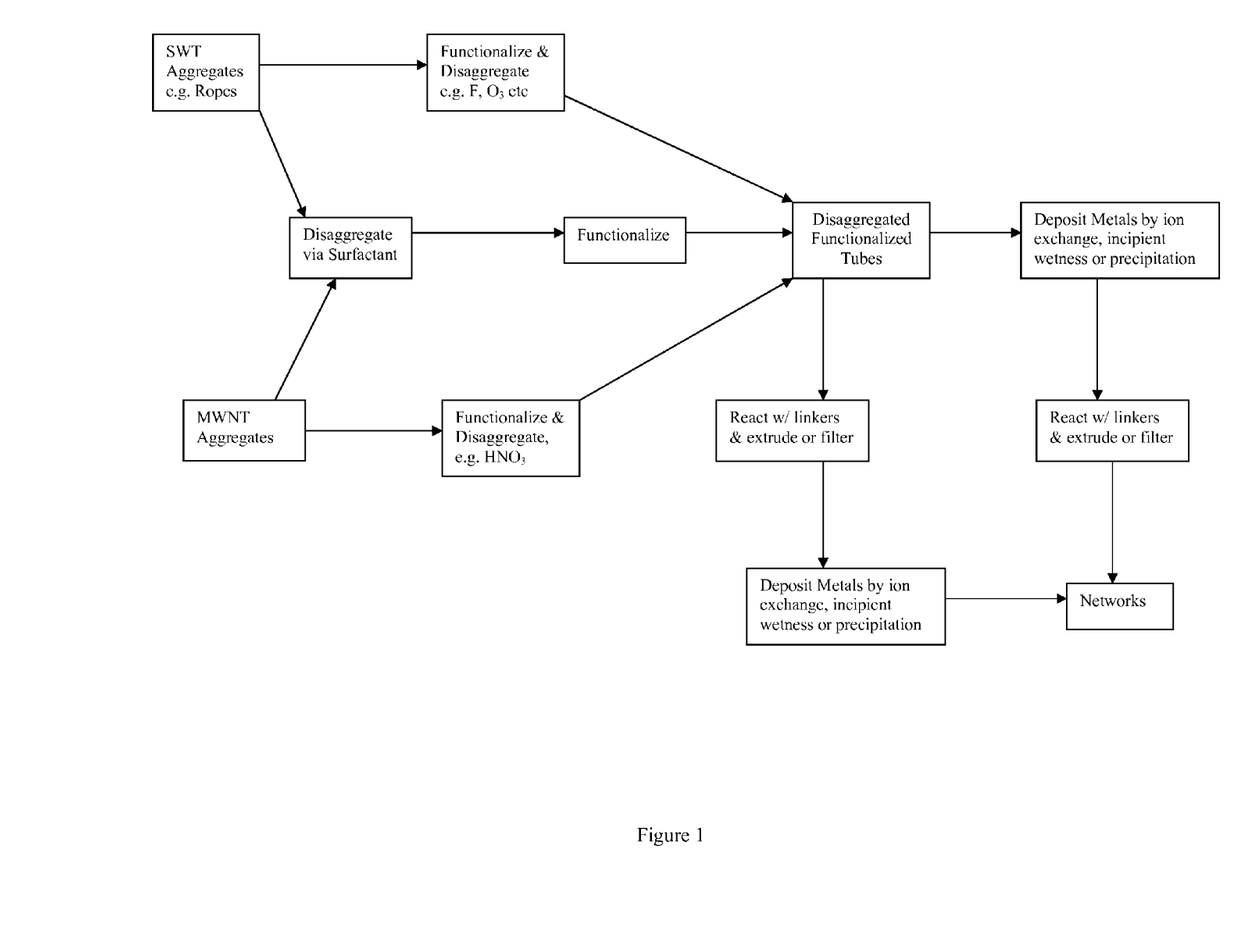
FIG. 1 is a flow chart illustrating the various embodiments of the present invention.

All patents, patent applications, and patent publications referred to herein are incorporated by reference in their entirety.

Definitions

The terms "nanotube", "nanofiber" and "fibril" are used interchangeably to refer to single walled or multiwalled carbon nanotubes. Each refers to an elongated structure preferably having a cross section (e.g., angular fibers having edges) or a diameter (e.g., rounded) less than 1 micron (for multiwalled nanotubes) or less than 5 nm (for single walled nanotubes). The term "nanotube" also includes "buckytubes", and fishbone fibrils.

"Aggregate" refers to a dense, microscopic particulate structures of entangled carbon nanotubes.

"Assemblage" refers to structures having relatively or substantially uniform physical properties along at least one dimensional axis and desirably having relatively or substantially uniform physical properties in one or more planes within the assemblage, i.e., they have isotropic physical properties in that plane. The assemblage may comprise uniformly dispersed individual interconnected nanotubes or a mass of connected aggregates of nanotubes. In other embodiments, the entire assemblage is relatively or substantially isotropic with respect to one or more of its physical properties. The physical properties which can be easily measured and by which uniformity or isotropy are determined include resistivity and optical density.

"Graphenic" carbon is a form of carbon whose carbon atoms are each linked to three other carbon atoms in an essentially planar layer forming hexagonal fused rings. The layers are platelets having only a few rings in their diameter or ribbons having many rings in their length but only a few rings in their width.

"Graphitic" carbon consists of layers which are essentially parallel to one another and no more than 3.6 angstroms apart.

"Internal structure" refers to the internal structure of a carbon nanotube structure including the relative orientation of the carbon nanotubes, the diversity of and overall average of nanotube orientations, the proximity of the nanotubes to one another, the void space or pores created by the interstices and spaces between the fibers and size, shape, number and orientation of the flow channels or paths formed by the connection of the void spaces and/or pores. According to another embodiment, the structure may also include characteristics relating to the size, spacing and orientation of aggregate particles that form the assemblage. The term "relative orientation" refers to the orientation of an individual nanotube or aggregate with respect to the others (i.e., aligned versus non-aligned). The "diversity of" and "overall average" of nanotube or aggregate orientations refers to the range of nanotube orientations within the structure (alignment and orientation with respect to the external surface of the structure).

"Isotropic" means that all measurements of a physical property within a plane or volume of the structure, independent of the direction of the measurement, are of a constant value. It is understood that measurements of such non-solid compositions must be taken on a representative sample of the structure so that the average value of the void spaces is taken into account.

"Macropore" refers to a pore which has a diameter of greater than or equal to 50 nm.

"Mesopore" refers to a pore which has a diameter of greater than or equal to 2 nm but less than 50 nm.

"Micropore" refers to a pore which has a diameter of less than 2 nm.

"Nonuniform pore structure" refers to a pore structure occurring when individual discrete nanotubes are distributed in a substantially nonuniform manner with substantially nonuniform spacings between nanotubes.

"Physical property" means an inherent, measurable property of the porous structure, e.g., surface area, resistivity, fluid flow characteristics, density, porosity, etc.

"Pore" traditionally refers to an opening or depression in the surface of a catalyst or catalyst support. Catalysts and catalyst supports comprising carbon nanotubes lack such traditional pores. Rather, in these materials, the spaces between individual nanotubes behave as (and are referred to herein as) pores, and the equivalent pore size of nanotube aggregates can be measured by conventional methods (porosimetry) of measuring pore size and pore size distribution. By varying the density and structure of aggregates, the equivalent pore size and pore size distribution can be varied.

"Relatively" means that 95% of the values of the physical property when measured along an axis of, or within a plane of or within a volume of the structure, as the case may be, will be within plus or minus 20% of a mean value.

"Substantially" or "predominantly" mean that 95% of the values of the physical property when measured along an axis of, or within a plane of or within a volume of the structure, as the case may be, will be within plus or minus 10% of a mean value.

"Surface area" refers to the total surface area of a substance measurable by the BET technique as known in the art, a physisorption technique. Nitrogen or helium can be used as absorbents to measure the surface area.

"Uniform pore structure" refers to a pore structure occurring when individual discrete nanotubes or nanofibers form the structure. In these cases, the distribution of individual nanotubes in the particles is substantially uniform with substantially regular spacings between the nanotubes. These spacings (analogous to pores in conventional supports) vary according to the densities of the structures.

Methods Of Preferred Embodiments

The present invention provides a new process for preparing supported catalysts comprising a metal loaded carbon nanotube network structure. The supported catalysts prepared in accordance with the preferred embodiment results in a better distribution and better dispersion of the metal catalysts within the carbon nanotube network structure, and consequently can yield better catalytic activity.

In a preferred embodiment, the method comprises loading the metal catalyst onto carbon nanotubes and forming a carbon nanotube network structure from the loaded carbon nanotubes. Preferably, the carbon nanotubes are functionalized before loading the metal catalysts.

In a preferred alternative embodiment, the method comprises loading the metal catalyst onto carbon nanotube network structures after the network structure has been formed.

As used throughout this application, the term "metal catalyst" includes precursors of such metal catalyst. That is, metal catalyst includes metals such as ruthenium, osmium, rhodium, iridium, palladium, platinum or a mixture thereof, as well as precursors of other transition metals such as metal oxides, metal halides, metal carbides, metal nitrides, metal phosphides and metal sulfides sulfides of metals including but not limited to Ti, V, Cr, Mn, Fe, Co, Ni, Cu, Zn, Y, Zr, Nb, Mo, La, Ce, W or combinations thereof The carbon nanotube network structure containing the metal catalysts represent the supported catalyst. When metal catalysts (in the form of precursors of metal catalyst) are loaded onto the carbon nanotube, various treatments such as calcinations, reduction, carburization, nitridization, phosphurization and sulphurization can be applied to obtain the desired catalyst composition.

As such, the terms supported catalyst and supported metal catalyst as used in this application may refer to any of the inert support with metal salt (or active material precursor) deposited thereon; the same material after calcination or other pre-reaction treatment; or the inert support with active material thereon having whatever composition it takes on in the reaction zone.

Functionalization

In a preferred embodiment, carbon nanotubes (whether produced in the form of discrete nanotubes or as-made aggregates, or mixture of both) are predeposited or loaded with metal catalysts before the metal loaded carbon nanotubes are made into a carbon nanotube network structure. All types of carbon nanotubes, whether single walled or multi walled, can be used.

A preferred method to accomplish the predeposition or loading of the metal catalyst onto the carbon nanotube is to first functionalize the carbon nanotube surface before mixing with the metal catalyst or salt thereof. Functionalizing the carbon nanotubes results in the substitution of functional groups such as oxygen containing moieties onto the surface of the carbon nanotubes, which consequently results in better attachment of the metal catalyst to the carbon nanotube surface (whether by adsorption, hydrogen bond, adhesion, electrostatic attraction, covalent bond, absorption, van der Waals force, or any other mechanism which may occur to secure, support, hold or otherwise keep the metal catalyst onto the carbon nanotube surface). A decent survey article on functionalization, hereby included in its entirety by reference, discussing single wall and multi walled carbon nanotubes is Hirsch, A. and Vostrowsky, O., "Functionalization of Carbon Nanotubes", Topics in Current Chemistry, (2005) 245: 193-237.

Functionalization can be accomplished, for example, by contacting the carbon nanotubes with an appropriate reagent (e.g., WO 97/32571, U.S. Pat. No. 6,203,814, all of which are herein incorporated by reference), or preferably by contacting them with an oxidizing agent such as potassium chlorate, sulfuric acid, nitric acid ($HNO_3$), persulfate, hydrogen peroxide ($H_2O_2$), $CO_2$, $O_2$, steam, $N_2O$, NO, $NO_2$, $O_3$, $ClO_2$, etc. (e.g., U.S. Pat. No. 5,965,470, WO 95/07316, PCT/US00/18670 or WO 01/07694, all of which are herein incorporated by reference).

Where the carbon nanotubes are in the form of aggregates, it is preferred to both break up or de-aggregate the aggregates and functionalize them. Such tasks can be accomplished concurrently by oxidizing the carbon nanotube aggregates, for example, by contacting them with an oxidizing agent such as potassium chlorate, sulfuric acid, nitric acid ($HNO_3$), persulfate, hydrogen peroxide ($H_2O_2$), $CO_2$, $O_2$, steam, $N_2O$, NO, $NO_2$, $O_3$, $ClO_2$, etc. (e.g., U.S. Pat. No. 5,965,470, WO 95/07316, PCT/US00/18670 or WO 01/07694, all of which are herein incorporated by reference). Breaking up of the as-produced aggregates into individual carbon nanotubes is preferable (although not necessary) in order to permit a more thorough distribution of functional groups onto the carbon nanotube surfaces, as well as to easier facilitate the creation of the carbon nanotube network structures. Hence, when oxidizing agents are used, the terms "functionalized" and "oxidized" may be used interchangably.

In an exemplary embodiment, the carbon nanotubes are oxidized by contacting the nanotubes with ozone under conditions suitable to achieve the desired functionalization (and deaggregation in the case of carbon nanotubes which are in the form of aggregates). Further details are provided in U.S. Provisional Application No. 60/621,132, filed Oct. 22, 2004 entitled "OZONOLYSIS OF CARBON NANOTUBES," herein incorporated by reference.

A particularly useful functionalization method especially for single wall tubes is cycloaddition. See, for example, Holzinger, M., et al., "[2+1] cycloaddition for cross linking SWCNTs", Carbon 42 (2004) 941-947, and Georgakilas, V., etal., "Organic Functionalization of Carbon Nanotubes", JACS Communications, 124 (2002) 760, 761, both of which are hereby included by reference. Alternatively, single wall tubes can be functionalized as described in U.S. Ser. No. 10/875435 filed Jun. 23, 2004, hereby incorporated by reference.

The functional groups which remain after the deposition or loading of the metal catalyst permit the individual carbon nanotubes to form carbon nanotube network structures with a linking molecule between the functionalized groups located on the surface of the carbon nanotubes. (E.g., PCT/US97/03553 or WO 97/32571, hereby incorporated by reference).

Predeposition Or Loading Of Metal Catalysts

Preferred metal catalysts include ruthenium, osmium, rhodium, iridium, palladium, platinum or a mixture thereof, as well as metal oxides, metal halides, metal carbides, metal nitrides, metal phosphides and metal sulfides of other transition metals including Ti, V, Cr, Mn, Fe, Co, Ni, Cu, Zn, Y, Zr, Nb, Mo, La, Ce, W or combination thereof More preferably, the metal catalyst is palladium, platinum, or a mixture thereof Where the carbon nanotubes are previously functionalized, predeposition or loading of the metal catalyst onto the carbon nanotube surface can be accomplished by mixing the metal catalyst material with the carbon nanotubes. Due to the change in carbon nanotube surface chemistry caused by the presence of functional groups, the metal catalyst may be held or supported onto the carbon nanotube surface via adsorption, hydrogen bond, adhesion, electrostatic attraction, covalent bond, absorption, van der Waals force or any other mechanism which may occur to secure, support, hold or otherwise keep the metal catalyst onto the carbon nanotube surface. It is preferred, where the functional groups are used to subsequently link the individual nanotubes to form carbon nanotube structures, that the amount of metal deposited or loaded onto the carbon nanotube surface not exceed or otherwise "use up" the functional groups needed to hold or support the metal catalyst on the carbon nanotube surface. In other words, it is preferred that there be free functional groups remaining on the carbon nanotube surface after the predeposition or loading of the metal catalyst.

Furthermore, the metal catalysts can be introduced to the carbon nanotubes in the form of a salt or derivative, or in the form of metal-containing micelles. As discussed earlier, these forms are often referred to as precursors of the metal catalyst, but are included in the term metal catalysts as used in this application. For example, the metal can be introduced to the carbon nanotube in the form of a water-soluble salt such as nitrate, acetate or chloride. Metal catalysts which have been loaded onto the carbon nanotube as salts are then preferably reduced via a reducing agent to further accomplish the deposition of the metal catalyst onto the carbon nanotube surface. Additionally, it is preferred in the case of metal catalysts introduced as a metal salt in a solution, that the solvent component of the solution be subsequently evaporated.

Any conventional mixing devices or mechanism can be employed. Factors such as mixing speed or time can be adjusted accordingly to facilitate the contact of the carbon nanotube and the metal catalyst, and to spread the metal catalyst thoroughly throughout the mixture so as to create a better distribution of metal catalysts on the carbon nanotubes.

Additional methods for accomplishing predeposition of the metal catalyst onto the carbon nanotube surface include, but is not limited to, impregnation, incipient wetness, ion exchange, precipitation, physical or chemical adsorption and co-precipitation.

Carbon nanotubes which have metal catalysts deposited on them will be referred to as "predeposited carbon nanotubes" or "metal loaded carbon nanotubes."

Carbon Nanotube Network Structures

Once the metal catalysts have been deposited onto the surfaces of the carbon nanotubes, these metal loaded carbon nanotubes are then used to form the carbon nanotube network structures using conventional methods as previously described.

Preferably, the metal loaded carbon nanotubes are functionalized, for example, by contacting them with an appropriate reagent such as those described in WO 97/32571 or U.S. Pat. No. 6,203,814, all of which are incorporated by reference. Alternatively, the metal loaded carbon nanotubes are functionalized through oxidation with oxidizing agents such as potassium chlorate ($KClO_3$), sulfuric acid ($H_2SO_4$), nitric acid ($HNO_3$), hydrogen peroxide ($H_2O_2$), $CO_2$, $O_2$, steam, $N_2O$, NO, $NO_2$, $O_3$, $ClO_2$, etc. (e.g., U.S. Pat. No. 5,965,470, WO 95/07316, PCT/US00/18670 or WO 01/07694, all of which are herein incorporated by reference). Typical linking molecules are bifunctional compounds such as diamines, diols, etc.

In accordance with a preferred embodiment, because the metal catalysts have already been deposited, spread and distributed throughout the carbon nanotubes in its discrete form prior to creating the carbon nanotube network structure, the result is that the carbon nanotube network structure itself would also have a greater and/or more even distribution of metal catalyst throughout and within the network structure. Furthermore, because of the porosity characteristics (e.g., more meso and macropores) of the carbon nanotube network structure, the accessibility and availability of the metal catalyst for reactions is greater than in other support catalyst structures previously prepared. This availability improvement is especially significant for liquid phase reactions, where larger pores are needed in order for the liquid phase reactants to reach the internal metal catalysts.

In a preferred alternative embodiment, the carbon nanotube structures may be formed first before loading the metal catalyst. Thus, the carbon nanotubes are functionalized, for example, by contacting them with an appropriate reagent such as those described in WO 97/32571 or U.S. Pat. No. 6,203,814, all of which are incorporated by reference. Alternatively, the carbon nanotubes are functionalized through oxidation with oxidizing agents such as potassium chlorate ($KClO_3$), sulfuric acid ($H_2SO_4$), nitric acid ($HNO_3$), hydrogen peroxide ($H_2O_2$), $CO_2$, $O_2$, steam, $N_2O$, NO, $NO_2$, $O_3$, $ClO_2$, etc. (e.g., U.S. Pat. No. 5,965,470, WO 95/07316, PCT/US00/18670 or WO 01/07694, all of which are herein incorporated by reference). Linking molecules such as bifunctional compounds such as diamines, diols, etc. are then added to form the carbon nanotube network structure. Once formed, the metal catalyst are loaded onto the carbon nanotube network structure using any of the loading/deposition processes previously discussed (e.g., ion exchange, impregnation, or incipient wetness, precipitation, physical or chemical adsorption or co-precipitation, etc.)

These catalytic compositions can be used as catalysts to catalyze reactions such as hydrogenation, hydrodesulfurisation, hydrodenitrogenation, hydrodemetallisation, hydrodeoxygenation, hydrodearomatization, dehydrogenation, hydrogenolysis, isomerization, alkylation, dealkylation, transalkylation, hydroformylation, water-gas shift, Fischer-Tropsch, COx-free hydrogen production, ammonia synthesis, electrocatalysis, oxidation, florination, and $NO_x$ reduction.

EXAMPLES

The examples are illustrative and not to be considered restrictive of the scope of the invention. Numerous changes and modification can be made with respect to the invention. The materials used in the examples herein are readily commercially available.

In all of the experiments which follow, aggregates of carbon nanotubes as manufactured by Hyperion Catalysis International of Cambridge, Mass. were used. The aggregates of carbon nanotubes were of the cotton candy ("CC") morphology also known as combed yarn ("CY").

Example 1

Carbon Nanotube Network

A covalently linked, carbon nanotube network is prepared by coupling a plurality of nanotubes together with molecules of a polyfunctional linker. The linker can have two or more reactive groups that are either the same or different such that at least one functional group on a linker molecule will react with one nanotube and at least a second functional group on the same linker molecule can react with a second nanotube thereby covalently linking the two nanotubes together. The functional groups on the polyfunctional linker can be the same or different and can be selected to react directly with an unfunctionalized nanotubes or selected to react with functional groups already present on the nanotubes.

Carbon nanotubes with carboxyl functional groups are linked using a diamine linker. Carbon nanotubes are slurried in 6M nitric acid in a two-necked, round bottom flask. The flask is fitted with a condenser with a water jacket in one neck and an overhead stirrer with a Teflon blade in another neck. The slurry is set to stirring and heated to reflux for 1-24 hours during which the nanotubes are oxidized forming carboxyl and other oxygen containing functional groups. The degree of functionalization is assayed by acid base titration. The carboxyl groups may be predominantly on the ends of the nanotubes or, especially in the case of MWNT, at sites on the sidewalls of the nanotubes.

Carboxylated nanotubes are activated to an N-hydroxysuccinimide (NHS) ester by carbodiimide coupling using 1-ethyl-3(3-dimethylaminopropyl)-carbodiimide. The nanotubes are then washed with dioxane and methanol then dried under vacuum to yield NHS ester-activated nanotubes.

NHS ester-activated nanotubes are cross-linked by the diamine, ethylenediamine, by adding ethylenediamine in 0.2M $NaHCO_3$ to form a concentrated slurry or paste to maintain a large number of nanotube to nanotube contacts where linkage can take place. The linking reaction is carried out for 4 hours at room temperature. The resulting linked network of nanotubes is washed with water, methanol, ethyl acetate, methanol, water and sodium bicarbonate (0.2 M, pH 8.0). Finally the filter cake can form either a mat via filtration or extrudate via extrusion as disclosed elsewhere.

Example 2

Carbon Nanotube Network Supported Catalyst via Post-network Deposition

Functionalized carbon nanotubes contain a variety of diverse functional groups, i.e. anionic (e.g. —$SO_3H$, —COOH), cationic (e.g. —$N(R_1, R_2, R_3)^+$ or more or less complex organic groups like amino, amide, ester, nitrile, epoxy or other reactive centers. Preparation of a metal loaded carbon nanotube composite can then be carried out by the preparation of functionalized carbon nanotubes, metallation either by ion-exchange or impregnation with a metal compound and the reduction of metal compound to metallic state.

30 ml 0.25 wt % $PdCl_2$/HCl solution is loaded in a flask with 20 ml water. The pH of the solution at this point is around 4. 1.001 g of CNT mat containing carbon nanotube network made in Example 1 are added to the solution. The slurry is stirred at room temperature for 24 hours. The filtration of the slurry yielded a light yellow filtrate, indicating that not all of the Pd ions are loaded on the surface of fibril. After thoroughly washed with DI water, the cake is dried at 110° C. in vacuum over night.

It was found that the metal loading was 3 wt % at most for loading palladium on carbon nanofibers with ion-exchange (M. L. Toebes, F. F. Prinsloo, J. H. Bitter, A. J. van Dillen and K. P. de Jong, "*Synthesis and characterization of carbon nanofiber supported ruthenium catalysts*", in *Studies in Surface Science and Catalysis*, vol. 143, P202). Therefore, the CO chemisorption for the sample reduced with $H_2$ at 300° C. for 2 hr shows that the Pd dispersion and particle size is 33.4% and 3.4 nm, if assuming 3 wt % of Pd loading.

Example 3

Carbon Nanotube Network Supported Catalyst via Pre-network Deposition

Metal catalyst can also be pre-deposited on functionalized carbon nanotubes via ion-exchange or impregnation pathways. A Pd catalysts supported on carbon nanotubes is prepared by incipient wetness impregnation. First, 10 grams of CC-type carbon nanotubes are placed in a 250-cc round bottom flask and oxidized by 63% nitric acid under reflux condition for four hours. After thorough washing with de-ionized water, the oxidized nanotubes are impregnated with $Pd(NO_3)_2$/acetone solution to yield a metal loading of 5%.

Pd-loaded nanotubes are then activated to an N-hydroxysuccinimide (NHS) ester by carbodiimide coupling using 1-ethyl-3(3-dimethylaminopropyl)-carbodiimide. The product is then washed with dioxane and methanol then dried under vacuum to yield NHS ester-activated nanotubes.

NHS ester-activated nanotubes are cross-linked by the diamine, ethylenediamine, by adding ethylenediamine in 0.2M $NaHCO_3$ to form a concentrated slurry or paste to maintain a large number of nanotube to nanotube contacts where linkage can take place. The linking reaction is carried out for 4 hours at room temperature. The resulting linked network of nanotubes is washed with water, methanol, ethyl acetate, methanol, water and sodium bicarbonate (0.2 M, pH 8.0). Finally the filter cake can form either a mat via filtration or extrudate via extrusion as disclosed elsewhere.

The CO chemisorption for the sample reduced with $H_2$ at 300° C. for 2 hr showed that the Pd dispersion and particle size is 44% and 2.5 nm.

Example 4

Hydrogenation of Nitrobenzene on a Carbon Nanotube Network Supported Catalyst

Hydrogenation of nitrobenzene is generally agreed as a strong exothermic reaction and very fast on many metals. The process is usually limited by diffusion. When carbon nanotube network serves as a catalyst support, the diffusion limitation created by micropores of amorphous carbon when activated carbon was used as support is eliminated. Thus such catalyst provides a better performance when compared with a conventional activated carbon or carbon black supported catalyst.

The reaction is carried out at ambient temperature and pressure in a three-neck round bottom flask with overhead stirrer. 0.050 g of catalyst made from Example 2 is placed in the flask with 50 ml isopropanol. Before adding the reactant, the catalyst is in-situ reduced by bubbling hydrogen for two hours under agitation. 50 ml of 10 vol % nitrobenzene in 2-propanol is added to the slurry. Small amount of sample is taken out every 30 min (every 15 min in the first 45 min) by using a syringe equipped with a filter until nitrobenzene consumed completely, which is determined by a GC equipped with FID and 3% OV-17/Chromosorb W-HP column. The conversion of nitrobenzene is found to reach 100% after 180 minutes.

The terms and expressions which have been employed are used as terms of description and not of limitations, and there is no intention in the use of such terms or expressions of excluding any equivalents of the features shown and described as portions thereof, it being recognized that various modifications are possible within the scope of the invention.

Thus, while there had been described what are presently believed to be the preferred embodiments of the present invention, those skilled in the art will appreciate that other and further modifications can be made without departing from the true scope of the invention, and it is intended to include all such modifications and changes as come within the scope of the claims.

We claim:

1. A method for preparing a supported catalyst comprising the steps of:
    de-aggregating aggregates of carbon nanotubes to provide de-aggregated carbon nanotubes;
    functionalizing said de-aggregated carbon nanotubes to provide functionalized carbon nanotubes;
    loading metal catalysts onto said functionalized carbon nanotubes to provide metal loaded carbon nanotubes; and
    forming a carbon nanotube network structure from said metal loaded carbon nanotubes with a linking agent.

2. The method of claim 1, wherein said metal catalyst is selected form the group consisting of ruthenium, osmium, rhodium, iridium, palladium, platinum, or metal oxides, metal halides, metal carbides, metal nitrides, metal phosphides and metal sulfides of Ti, V, Cr, Mn, Fe, Co, Ni, Cu, Zn, Y, Zr, Nb, Mo, La, Ce, W or combination thereof.

3. The method of claim 1, wherein the steps of de-aggregating and functionalizing are accomplished concurrently by oxidizing said aggregates.

4. The method of claim 3, wherein oxidizing said aggregates comprises contacting said aggregates with an oxidizing agent selected from the group consisting of potassium chlorate, sulfuric acid, $HNO_3$, persulfate, $H_2O_2$, $CO_2$, $O_2$, steam, $N_2O$, NO, $NO_2$, $O_3$, and $ClO_2$.

5. The method of claim 3, wherein oxidizing said aggregates comprises contacting said aggregates with an oxidizing agent selected from the group consisting of $CO_2$, $O_2$, steam, and $O_3$.

6. The method of claim 1, wherein said linking agent comprises a diamine linking agent.

7. The method of claim 6, wherein said diamine linking agent comprises ethylenediamine.

8. The method of claim 6, wherein said functionalized carbon nanotubes comprise carboxylated carbon nanotubes.

9. The method of claim 6, wherein said functionalized carbon nanotubes comprise N-hydroxysuccinimide ester-activated carbon nanotubes.

10. The method of claim 9, wherein said functionalized carbon nanotubes comprise carboxylated carbon nanotubes, and further wherein said N-hydroxysuccinimide ester-activated carbon nanotubes are formed by activating said carboxylated carbon nanotubes to an N-hydroxysuccinimide ester.

11. The method of claim 10, wherein said activating said carboxylated carbon nanotubes to an N-hydroxysuccinimide ester comprises carbodiimide coupling using 1-ethyl-3(3-dimethylaminopropyl)-carbodiimide.

* * * * *